United States Patent
Benosman et al.

(10) Patent No.: US 10,500,397 B2
(45) Date of Patent: Dec. 10, 2019

(54) METHOD FOR DOWNSAMPLING A SIGNAL OUTPUTTED BY AN ASYNCHRONOUS SENSOR

(71) Applicants: UNIVERSITE PIERRE ET MARIE CURIE (PARIS 6), Paris (FR); CENTRE NATIONAL DE LA RECHERCHE SCIENTIFIQUE—CNRS, Paris (FR); INSERM (INSTITUT NATIONAL DE LA SANTE ET DE LA RECHERCHE MEDICALE), Paris (FR)

(72) Inventors: Ryad Benosman, Pantin (FR); Francesco Gallupi, Rome (IT); Guillaume Chenegros, Trappes (FR); Xavier Lagorce, Paris (FR); Christoph Posch, Vienne (AT)

(73) Assignees: SORBONNE UNIVERSITE, Paris (FR); CENTRE NATIONAL DE LA RECHERCHE SCIENTIFIQUE—CNRS, Paris (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 101 days.

(21) Appl. No.: 15/744,194

(22) PCT Filed: Jul. 18, 2016

(86) PCT No.: PCT/EP2016/067059
§ 371 (c)(1),
(2) Date: Jan. 12, 2018

(87) PCT Pub. No.: WO2017/013065
PCT Pub. Date: Jan. 26, 2017

(65) Prior Publication Data
US 2018/0207423 A1 Jul. 26, 2018

(30) Foreign Application Priority Data
Jul. 22, 2015 (EP) .................... 15306193

(51) Int. Cl.
*A61F 2/14* (2006.01)
*A61N 1/36* (2006.01)
(Continued)

(52) U.S. Cl.
CPC ............ *A61N 1/36046* (2013.01); *A61F 2/14* (2013.01); *G06N 3/049* (2013.01); *G06N 3/063* (2013.01);
(Continued)

(58) Field of Classification Search
CPC ............. G06T 5/00; G06T 2207/10016; G06T 2207/10141; A61F 9/08; A61F 2/14;
(Continued)

(56) References Cited

U.S. PATENT DOCUMENTS 9,846,677 B2 * 12/2017 Wang .................... G06F 17/141
2002/0050518 A1 * 5/2002 Roustaei ............ G06K 7/10544
235/454

(Continued)

FOREIGN PATENT DOCUMENTS

EP 2579575 A1 4/2013

OTHER PUBLICATIONS

Lagorce et al., "Spatiotemporal features for asynchronous event-based data", Frontiers in Neuroscience, Feb. 24, 2015, vol. 9.
(Continued)

*Primary Examiner* — Paul B Prebilic
(74) *Attorney, Agent, or Firm* — Young & Thompson

(57) ABSTRACT

Disclosed is a method for processing asynchronous signals generated by a light sensor, the sensor having a matrix of pixels, the method including: —receiving the asynchronous signals, each signal being associated with a pixel in a group of pixels in the matrix, each signal including successive events issued by the associated pixel; —upon an occurrence of an event in one of the asynchronous signals, updating an integration value associated to the group by adding an additive value to the integration value; —if the integration value is greater than a predetermined threshold, generating an event in an outputted asynchronous signal.

20 Claims, 7 Drawing Sheets

(51) Int. Cl.
*G06T 5/00* (2006.01)
*G06N 3/04* (2006.01)
*G06N 3/063* (2006.01)

(52) U.S. Cl.
CPC ...... *G06T 5/00* (2013.01); *G06T 2207/10016* (2013.01)

(58) Field of Classification Search
CPC .............. A61F 2/141; A61F 2250/0001; A61F 2250/0002; A61F 2250/0091
See application file for complete search history.

(56) References Cited

U.S. PATENT DOCUMENTS

| | | | |
|---|---|---|---|
| 2004/0169735 A1* | 9/2004 | Andersen | H04N 3/1587 348/219.1 |
| 2009/0312818 A1 | 12/2009 | Horsager et al. | |
| 2013/0335595 A1* | 12/2013 | Lee | H04N 5/23229 348/231.5 |
| 2014/0085447 A1* | 3/2014 | Lorach | A61N 1/0543 348/62 |
| 2014/0363049 A1 | 12/2014 | Benosman et al. | |
| 2015/0095818 A1* | 4/2015 | Lee | G06F 3/0488 715/765 |
| 2017/0053407 A1* | 2/2017 | Benosman | G06T 7/73 |
| 2018/0063449 A1* | 3/2018 | Sio-Hoi | G06K 9/6212 |

OTHER PUBLICATIONS

Benosman et al., "Event-Based Visual Flow", IEEE Transactions on Neural Networks and Learning Systems, Feb. 2014, pp. 407-417, vol. 25, No. 2.
Mathieson et al., "Photovoltaic retinal prosthesis with high pixel density", Nature Photonics, May 13, 2012, pp. 391-397, vol. 6, No. 6.
International Search Report, dated Oct. 21, 2016, from corresponding PCT application No. PCT/EP2016/067059.

* cited by examiner

METHOD FOR DOWNSAMPLING A SIGNAL OUTPUTTED BY AN ASYNCHRONOUS SENSOR

BACKGROUND OF THE INVENTION

The present invention relates to the down sampling of a signal issued from an asynchronous sensor especially for the inputting of the down sampled signal into a retinal prosthesis/a retina implant.

The approaches described in this section could be pursued, but are not necessarily approaches that have been previously conceived or pursued. Therefore, unless otherwise indicated herein, the approaches described in this section are not prior art to the claims in this application and are not admitted to be prior art by inclusion in this section. Furthermore, all embodiments are not necessarily intended to solve all or even any of the problems brought forward in this section.

Retinal prostheses hold the promise to partially restore visual functionality in subjects affected by retinal degenerative diseases.

However, state of the art implants only comprise a few hundreds pixels. Increasing the pixel density in implants is a very challenging process, and alternative techniques need to be exploited to compensate for reduced spatial resolution of said implants.

On the other hand, retina sensors (or asynchronous light sensors) may comprise thousands of pixels. Neuromorphic vision sensors (i.e. retina sensors/asynchronous sensors) asynchronously deliver streams of visual information with high time resolution, without the need to wait for a frame to be ready.

Sampling a scene to a lower resolution than the one captured by the retina sensors (cameras) is therefore a possible processing step.

The usual way to implement a down sampling (i.e. sampling a scene to a lower resolution) is to use the standard computer vision techniques that may be used with standard images/frames, etc.

However standard computer vision techniques (which handle frames) might not be the most adequate solution to deliver useful information to implanted patients. Indeed asynchronous information received from the retina sensors then need to be converted into 2D standard frames so that the usual method for down sampling may be used: this conversion may be processor consuming and time information may be lost.

There is thus a need for a method for down sampling a signal issued from asynchronous sensors without converting the signal into 2D (i.e. working directly in the asynchronous domain).

SUMMARY OF THE INVENTION

The invention relates to a method for processing asynchronous signals generated by a light sensor, the sensor having a matrix of pixels, the method comprising:
  receiving the asynchronous signals, each signal being associated with a pixel in a group of pixels in the matrix, each signal comprising successive events issued by the associated pixel;
  upon an occurrence of an event in one of the asynchronous signals, updating an integration value associated to said group by adding an additive value to the integration value;
  if the integration value is greater than a predetermined threshold, generating an event in an outputted asynchronous signal.

Light sensors that are able to generate asynchronous signals may be named "retina sensors" or "asynchronous sensors".

The events in the asynchronous signals are not synchronized by a clock (or the same). Therefore, a standard video sensor that generates frames (which are synchronous with a clock, e.g. 25 images per seconds) is not an asynchronous sensor.

The group of pixels may represent a subzone in the matrix of pixel (for instance a square or a rectangle).

Therefore, the method enables the generation of one flow of events (i.e. the outputted asynchronous signal) based on a plurality of received asynchronous signals. Therefore, it is possible to down sample signals outputted by a retina sensor in order to be inputted in a lower resolution device such as a retina implant.

The use of an integration value reproduce the behavior of the human neurons and thus the feeling of the implanted users are very close to what they are supposed to see with deficiencies.

In a possible embodiment, the method may further comprise:
  decreasing the integration value according to a time-dependent function.

Indeed, by decreasing the integration value (e.g. linear decay or exponential decay), it is possible to avoid that two distant events have the same effect than two close events. The behavior of human neurons is thus very similar.

Advantageously, the additive value may be one of:
  a predetermined value;
  a value function of:
    a predetermined value and
    a weighting parameter function of a position in the group of the pixel from which the occurred event is issued;
  a value function of an information of gray level associated with the occurred event;
  a value function of:
    an information of gray level associated with the occurred event; and
    a weighting parameter function of a position in the group of the pixel from which the occurred event is issued.

The weighting parameter enables the creation of recognition pattern ("kernel"). In addition such weighting parameter may enable to set a greater weight in the center of the group while the pixels near the edges of the group are disregarded. The output of such an operation can be fed in another kernel for performing further computation(s).

The information of gray level may be provided by the secondary signal outputted by an ATIS sensor (see below): the distance between two spikes may represent such gray level information.

In a possible embodiment, the method may further comprise sending the outputted asynchronous signal to a pixel of a retinal implant.

In addition, the method may further comprise, upon the generation of the event in the outputted signal, setting the integration value to 0 or upon the generation of the event in the outputted signal, setting the integration value to a value corresponding to the difference of the integration value and the predetermined threshold.

The difference between the integration value and the predetermined threshold may be performed directly or thanks to the computation of a modulo. By setting the integration value to a value corresponding to the difference of the integration value and the predetermined threshold, it is possible to avoid to "ignore" the portion of the integration value that exceeds the threshold. This may be particularly relevant if this portion is important.

In a specific embodiment, the predetermined threshold may be function of a number of pixels in the group of pixels.

Thus, if the group of pixels is large, it may be useful to set the threshold to a big value in order to avoid the generation of a too large number of events in the outputted signal (i.e. to avoid the saturation of the outputted signal). If the group of pixels is quite small, it may be useful to set the threshold to a small value in order to avoid a "blank" outputted signal.

A second aspect relates to a computer program product comprising a computer readable medium, having thereon a computer program comprising program instructions. The computer program is loadable into a data-processing unit and adapted to cause the data-processing unit to carry out the method described above when the computer program is run by the data-processing unit.

Still, analog implementation of such method is also possible. Therefore, an aspect of the invention may relate to a hardware device that enables an analog implementation of the above method.

Thus a third aspect relates to a retinal device comprising:
a light sensor, the sensor having a matrix of pixels,
an circuit, such as ASIC, for:
  receiving the asynchronous signals, each asynchronous signal being associated with a pixel in a group of pixels in the matrix, each signal comprising successive events issued by the associated pixel;
  upon an occurrence of an event in one of the asynchronous signals, updating an integration value associated to said group by adding an additive value to the integration value;
  if the integration value is greater than a predetermined threshold, generating an event in an outputted asynchronous signal.

Other features and advantages of the method and apparatus disclosed herein will become apparent from the following description of non-limiting embodiments, with reference to the appended drawings.

BRIEF DESCRIPTION OF THE DRAWINGS

The present invention is illustrated by way of example, and not by way of limitation, in the figures of the accompanying drawings, in which like reference numerals refer to similar elements and in which.

DESCRIPTION OF PREFERRED EMBODIMENTS

Figure 1A:
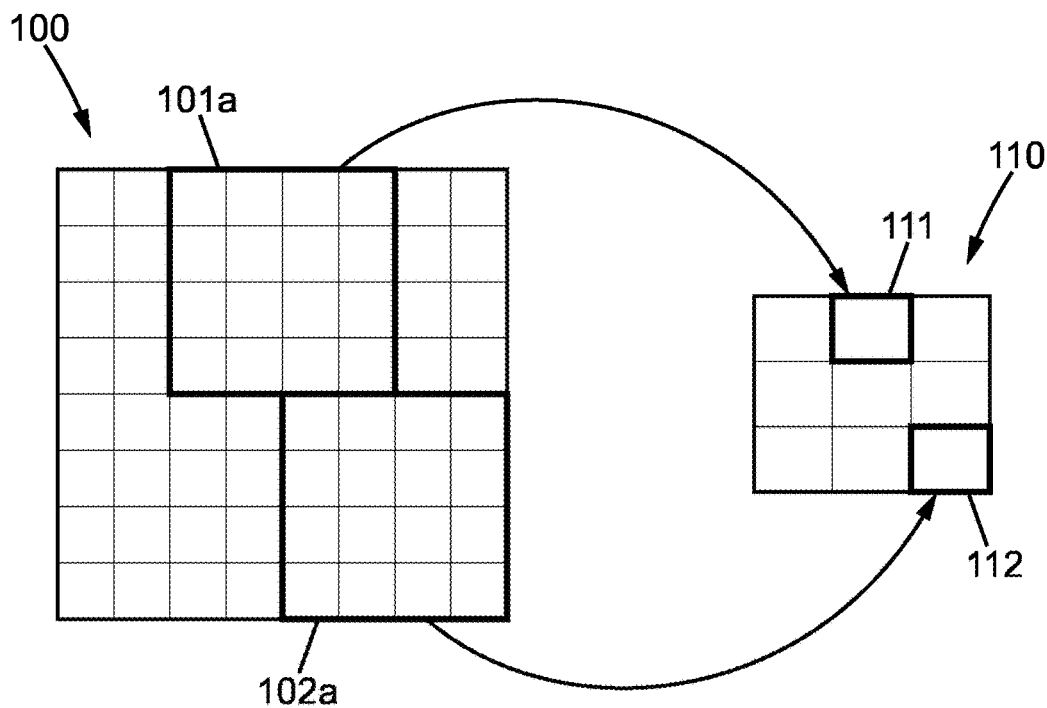
FIG. 1a and FIG. 1b are examples of various groups of pixels used for down sampling an input signal to an output down sampled signal.
Figure 1B:
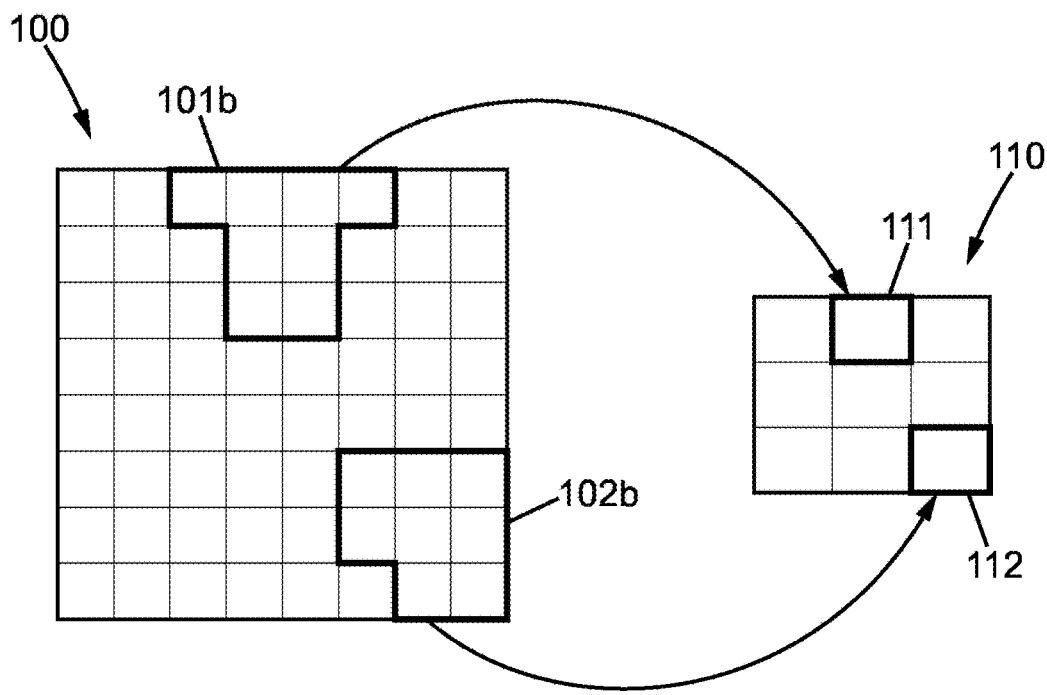

FIG. 1a and FIG. 1b are examples of various groups of pixels used for downsampling an input signal to an output downsampled signal.

As the retina sensor 100 comprises a greater number of pixels (8×8 in the present example) than the number of pixel of the retina implant 110 (3×3 in the present example), it is possible to compute events associated with each pixel of the retina implant (see FIG. 2 for the definition of an event in the context of a retina sensor or a retina implant) based on events of a plurality of pixels (most of the time, adjacent pixels) in the retina sensor 100.

For instance, in a possible embodiment, the events of the pixel 111 of the retinal implant may be determined based on the events that occur for the group of pixels 101a in the retina sensor. In a similar manner, the events of the pixel 112 of the retina implant may be determined based on the events that occur for the group of pixels 102a in the retina sensor.

It is noted that a same pixel of the retina sensor 100 may be used for two (or more) groups of pixels: indeed, an overlap between groups (101a, 102a) is acceptable.

In addition, any group of pixels may be of any forms. For instance, the events of group of pixels 101b (respectively 102b) may be used to compute the event of pixel 111 (respectively 112).

The influence of each pixel of a group may not be uniform for the computation of the events of the pixel in the retinal implant: for instance a pixel in the center of a group may have a greater impact of the computation than pixels on the edges of the group. To ease this embodiment, it is possible to receive a weighting matrix for each group that eases the determination of a weight w for each pixel in the group.

Figure 2:
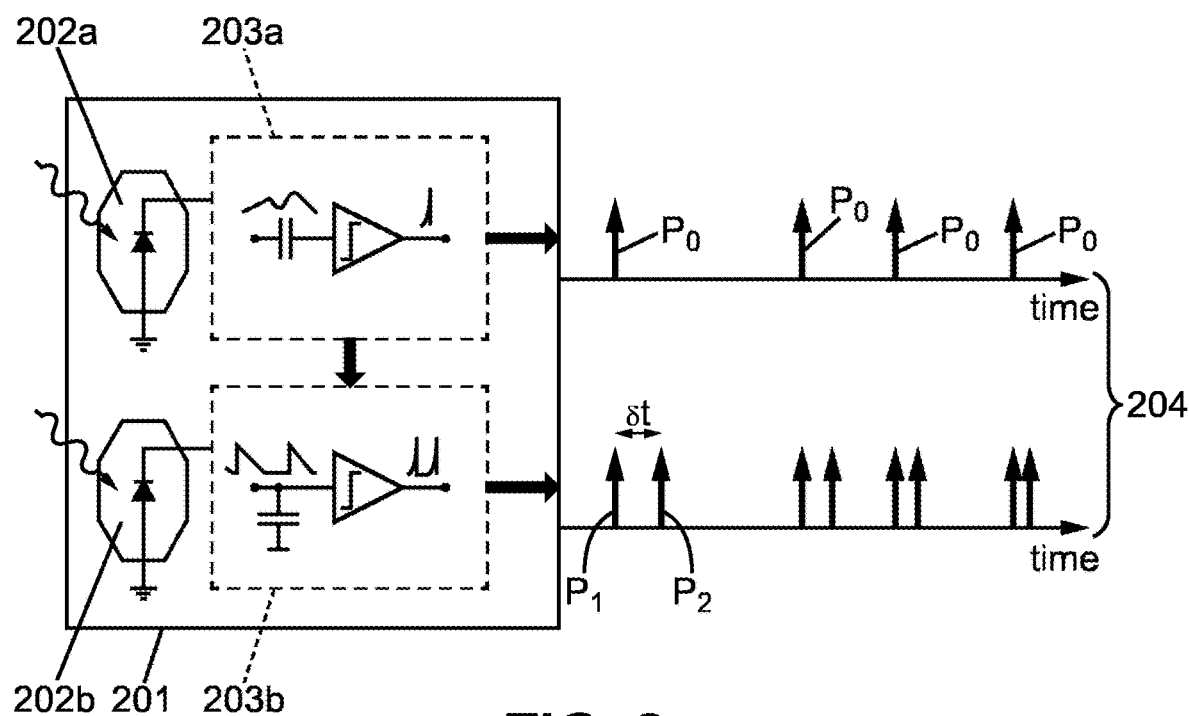
FIG. 2 is a representation of an ATIS sensor.

FIG. 2 is a representation of an asynchronous sensor.

A pixel 201 of the matrix constituting the sensor may include two photosensitive elements 202a, 202b, such as photodiodes, associated with respective electronic circuits of detection 203a, 203b.

If the pixel p only comprises the element 202a, the sensor is a classical asynchronous sensor. If the pixel comprises the two elements 202a and 202b, the sensor is an ATIS sensor.

The sensor 202a and the circuit 203a produce a pulse $P_0$ when the light intensity received by the photodiode 202 varies by a predetermined amount.

The asynchronous information from the standard sensor includes one pulse train $P_0$ indicating the times at which the light intensity has changed beyond the detection threshold: each single pulse may be then an "event" e(p, t).

$$e(p, t) = \begin{cases} p \in C \subset \mathbb{R}^2 \\ pol \end{cases}$$

with C the spatial domain of the retina sensor, pol the polarity of the change (e.g. 1 for an increase in the luminosity or −1 for a decrease).

If the sensor is an ATIS sensor, the pulse $P_0$ marking the change of intensity 203b triggers the electronic circuit associated with the other photodiode 202b. The circuit 203b then generates a first pulse $P_1$ and a second pulse $P_2$ when a quantity of light (e.g. number of photons) is received by the photodiode 202b.

The time difference δt between $P_1$ and $P_2$ pulses is inversely proportional to the light intensity received by the pixel 201 just after the occurrence of the pulse P0.

The asynchronous information from the ATIS includes two pulse trains combined for each pixel (204): the first train of pulses P0 indicates the instants at which the light intensity has changed beyond the detection threshold, while the second train comprises $P_1$ and $P_2$ pulses (δt time gap indicates the associated luminous intensities or gray levels).

For an ATIS sensor, the "event" may be defined as:

$$e(p, t) = \begin{cases} p \in C \subset \mathbb{R}^2 \\ pol \\ I(p, t) \end{cases}$$

with C the spatial domain of the retina sensor, pol the polarity of the change (e.g. 1 for an increase in the luminosity or −1 for a decrease) and I(p,t) the intensity variation (function of δt).

Figure 3A:
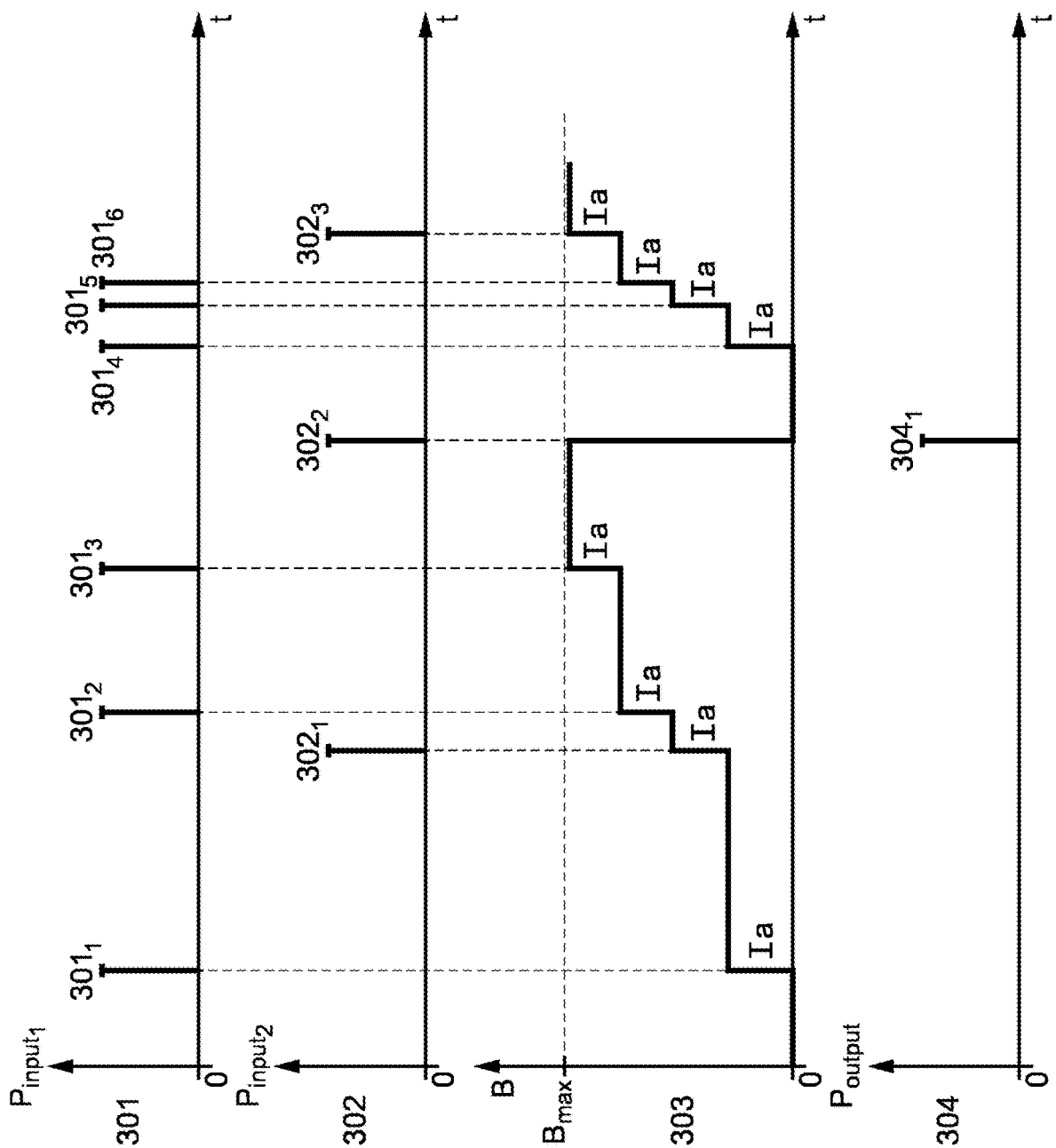
FIGS. 3a to 3c are examples of an integration process that may be used in an embodiment of the invention.
Figure 3B:
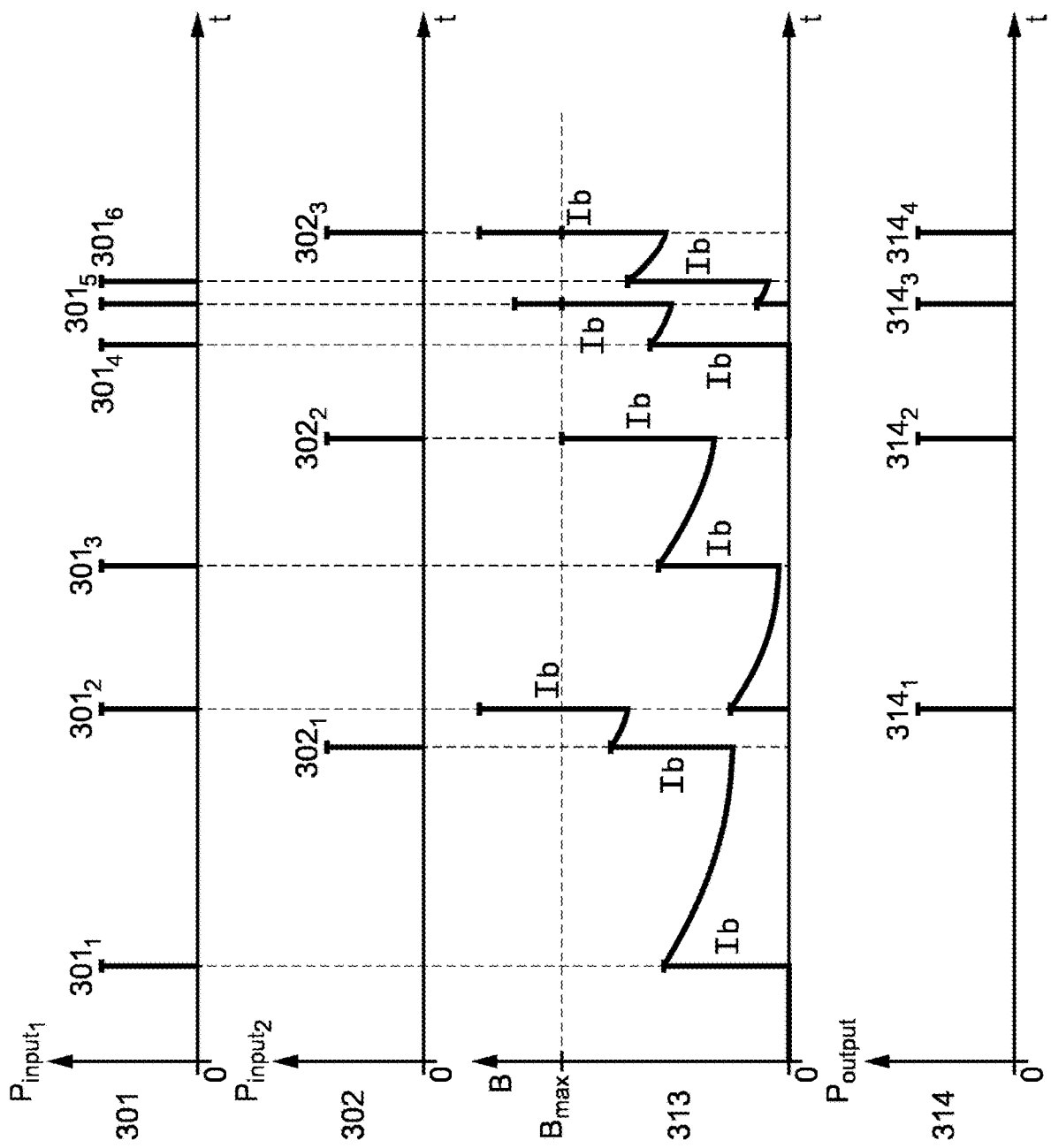
Figure 3C:
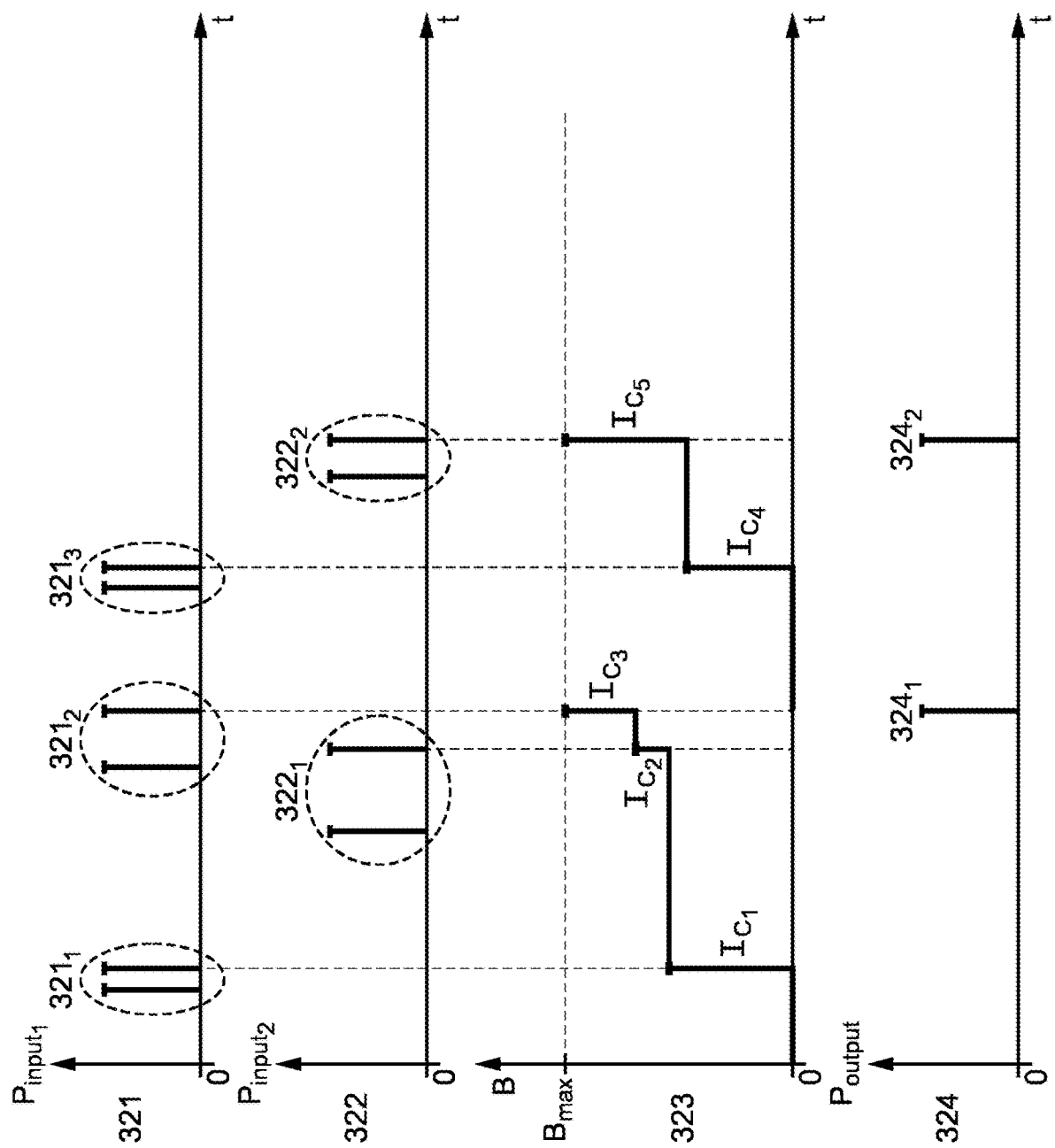

FIGS. 3a to 3c are examples of an integration process that may be used in an embodiment of the invention.

In the example of FIG. 3a, it is considered that the events of a group (e.g. 101a) of pixels of the retina sensor used to compute the events of a given pixel (e.g. 111) of the retinal implant are represented in graphs 301 and 302 by vertical spikes (the events are respectively {$301_1$, $301_2$, $301_3$, $301_4$, $301_5$, $301_6$} and {$302_1$, $302_2$, $302_3$} for the graph 301 and 302).

In FIG. 3a and for clarity reason, the group comprises only two pixels (i.e. only two graphs 301 and 302 are displayed). Nevertheless, the group may comprise a greater number of pixels.

The graph 303 represents an "integration" value B. In order to compute the integration value B in this embodiment, it is possible to initialize the value B to 0 and then to add a predetermined value $I_a$ each time an event is detected in a pixel of the group (i.e. when a spike is detected in graph 301 or 302). If the value of B is greater than a predetermined threshold $B_{max}$ (in the present FIG. 3a, when the spike $302_2$ occurs):

an output event is generated ($304_1$) and send to the retina implant to activate the pixel (of the retina implant) associated with said group (the signal sent to the pixel of the retina implant is represented by the graph 304);

the value of B is either reinitialized to 0 or the value of B is set to:

the difference between the former value of B and $B_{max}$ (i.e. the value of B is set to the former value of B exceeding $B_{max}$); or the value B modulo $B_{max}$ (i.e. the former value of B after the addition of $I_a$ modulo $B_{max}$).

In addition, it is possible to replace the addition of the predetermined value $I_a$ by an addition of a value function of the predetermined value $I_a$: for instance, if a weight w is determined according to a weighting matrix for a given pixel of the group (see above), the value added may be $w\,I_a$.

The value $B_{max}$ may be predetermined or determined based on the group of pixels (of the retina sensor) considered. For instance, the value $B_{max}$ may be a function of the number of pixels in said group (e.g. $B_{max}$ equals to the number of pixels multiplied by $I_a$).

In the example of FIG. 3b, it is considered that the events of a group (e.g. 101a) of pixels of the retina sensor used to compute the events of a given pixel (e.g. 111) of the retinal implant are represented in graphs 301 and 302 by vertical spikes (the events are respectively {$301_1$, $301_2$, $301_3$, $301_4$, $301_5$, $301_6$} and {$302_1$, $302_2$, $302_3$} for the graph 301 and 302).

In FIG. 3b and for clarity reason, the group comprises only two pixels (i.e. only two graphs 301 and 302 are displayed). Nevertheless, the group may comprise a greater number of pixels.

The graph 313 represents the "integration" value B. In order to compute the integration value B in this embodiment, it is possible to initialize the value B to 0 and then to add a predetermined value $I_b$ each time an event is detected in a pixel of the group (i.e. when a spike is detected in graph 301 or 302). If the value of B is greater than a predetermined threshold $B_{max}$ (in the present FIG. 3b, when respectively the spikes $301_2$, $302_2$, $301_5$, $302_3$ occur):

an output event is generated (respectively $314_1$, $314_2$, $314_3$, $314_4$) and send to the retinal implant to activate the pixel (of the retina implant) associated with said group (the signal sent to the pixel of the retina implant is represented by the graph 314). The event can also be sent to another computational layer before being sent to the retinal implant;

the value of B is either reinitialized to 0 or the value of B is set to:

the difference between the former value of B and $B_{max}$ (i.e. the value of B is set to the former value of B exceeding $B_{max}$); or the value B modulo $B_{max}$ (i.e. the former value of B after the addition of $I_a$ modulo $B_{max}$).

Furthermore, the value of B may not be constant when no event is detected for the pixels of the group. The value of B may decrease with time when no event is detected. This decay may be a linear decay, an exponential decay, or any other decay.

In addition, it is possible to replace the addition of the predetermined value $I_b$ by an addition of a value function of the predetermined value $I_b$: for instance, if a weight w is determined according to a weighting matrix for a given pixel of the group (see above), the value added may be $w\,I_b$.

The value $B_{max}$ may be predetermined or determined based on the group of pixels (of the retina sensor) considered. For instance, the value $B_{max}$ may be a function of the number of pixels in said group (e.g. $B_{max}$ equals to the number of pixels multiplied by $I_b$).

If the events received from the retina sensor are gray level events (i.e. sent by ATIS sensor as detailed above), it is possible to slightly adapt the integration process described in relation of FIG. 3a or FIG. 3b.

Indeed, each received event is not only represented by a single spike but by a couple of spikes. In the example of FIG. 3c, it is considered that the events of a group (e.g. 101a) of pixels of the retina sensor used to compute the events of a given pixel (e.g. 111) of the retinal implant are represented in graphs 321 and 322 by sets of two vertical spikes (the events are respectively {$321_1$, $321_2$, $321_3$} and {$322_1$, $322_2$} for the graph 321 and 322).

The graph 323 represents the "integration" value B. In order to compute the integration value B in this embodiment, it is possible to initialize the value B to 0 and then to add a value each time an event is detected in a pixel of the group (i.e. when the second spike of each sets of spikes is detected in graph 321 or 322): the added value may be function of the distance between the two spikes of the considered set.

For instance, the added value $I_{c1}$ is important as the distance between the two spikes of events $321_1$ is small. The added value $I_{c2}$ is small as the distance between the two spikes of events $322_1$ is important. Thus, the added value may be inversely proportional to the distance of the two spikes of the considered set.

If the value of B is greater than a predetermined threshold $B_{max}$ (in the present FIG. 3c, when respectively the events $321_2$, $322_2$ occur):

an output event is generated (respectively $324_1$, $324_2$) and sent to the retina implant to activate the pixel (of the retina implant) associated with said group of pixels (of the retina sensor) (the signal sent to the pixel of the retina implant is represented by the graph 324) or sent to another layer for performing further computation(s); the value of B is either reinitialized to 0 or the value of B is set to:

the difference between the former value of B and $B_{max}$ (i.e. the value of B is set to the former value of B exceeding $B_{max}$); or the value B modulo $B_{max}$ (i.e. the former value of B after the addition of $I_a$ modulo $B_{max}$).

Figure 4:
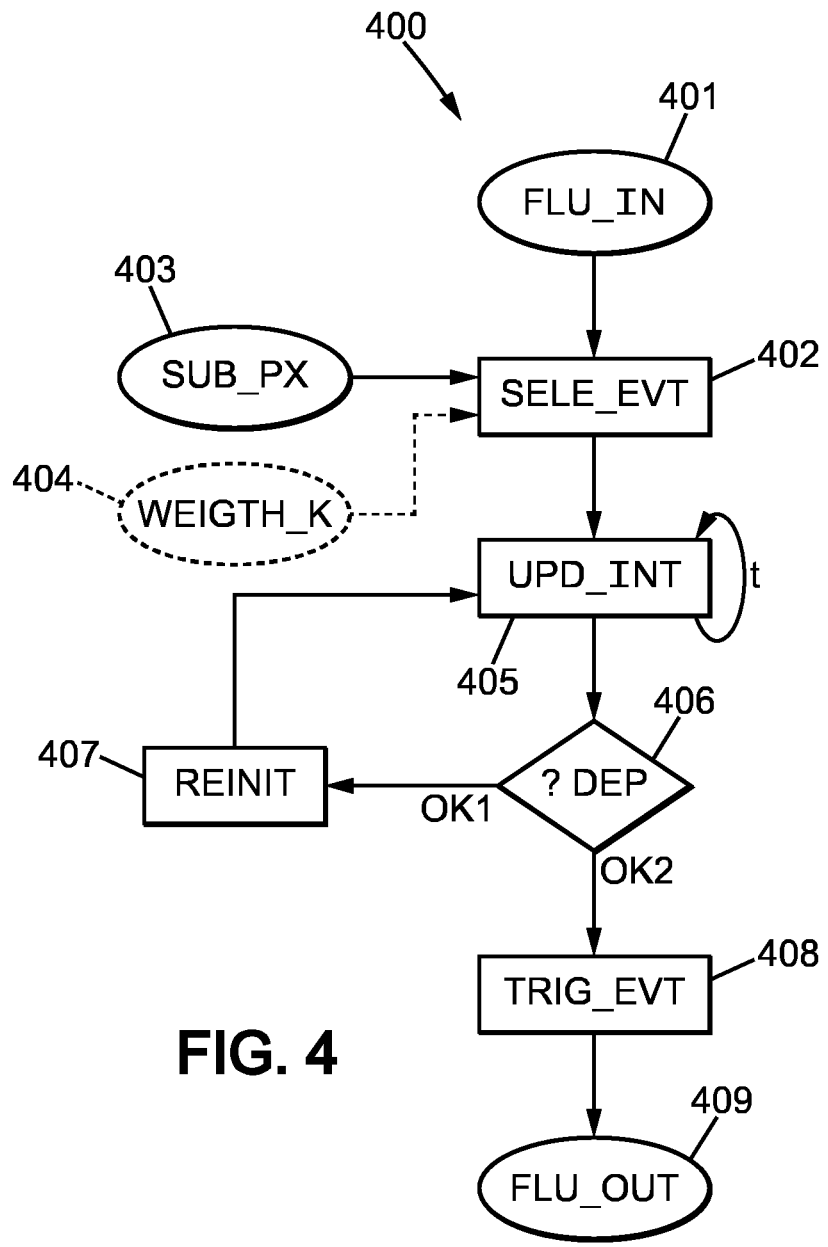
FIG. 4 is a flow chart describing a possible embodiment of the present invention.

FIG. 4 is a flow chart 400 describing a possible embodiment of the present invention.

When receiving an input signal 401 with a plurality of events for a plurality of pixels of a retina sensor, it is possible to select/filter (step 402) the events associated with a subpart 403 of pixels (i.e. a group) that are to be used for creating the events for a given pixel of the retina implant. Alternatively, it is possible to receive directly the events associated with the subpart of pixels (no filter is thus needed).

It is also possible to associate to said event a weight w, for instance based on the position of the pixel (from which the event is issued) in the group of pixels (e.g. based on a weighting matrix).

Once the events are filtered/selected, it is possible to update (step 405) an "integration value" as detailed in reference of FIG. 3a, 3b and/or 3c. The weight w may be used in this step. If the integration value is to be decreased with the time, it is possible to reiterate step 205 to decrease the integration value or to wait until the next event to update the value.

If the integration value computed in step 205 is greater than a predetermined value $B_{max}$ (which may be a function, e.g. a function of the number of pixels in the considered group) (test 406), then the integration value may be reinitialized as detailed in relation of FIG. 3a, 3b and/or 3c (test 406 output OK1, step 407) and an event may be generated (test 406 output OK2, step 408) in order to be inputted in the pixel of the retina implant associated with the considered group.

Thus, at the end, a new flow of events (409) is generated for a pixel of the retina implant based on the received flows (401) of events outputted by pixels of a given group in the retina sensor.

The flow chart of FIG. 4 may be executed in parallel for a plurality of groups of pixels of the retina sensor and for a plurality of pixels of the retina implant associated with said groups Part of this flow chart can represent steps of an example of a computer program which may be executed by a processor or a processing unit (e.g. an electronic circuit).

An (electronic) circuit may be for instance:

a processor or a processing unit adapted to interpret instructions in a computer language, the processor or the processing unit may comprise, may be associated with or be attached to a memory comprising the instructions, or the association of a processor/processing unit and a memory, the processor or the processing unit adapted to interpret instructions in a computer language, the memory comprising said instructions, or an electronic card wherein the steps of the invention are described within silicon, or a programmable electronic chip such as a FPGA chip (for "Field-Programmable Gate Array").

Figure 5C:
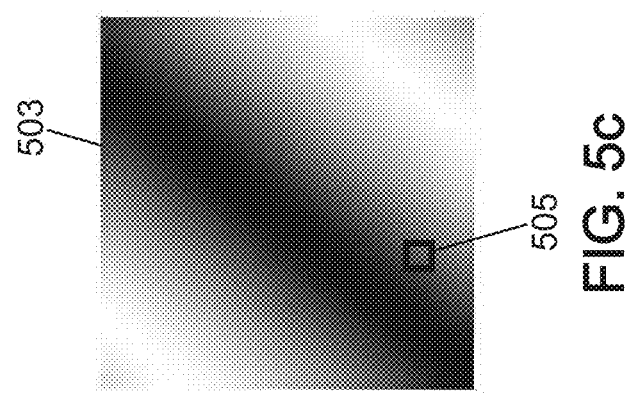
FIGS. 5a, 5b, and 5c are a set of examples of weighting matrix (or kernel) used in the integration process.
Figure 5B:
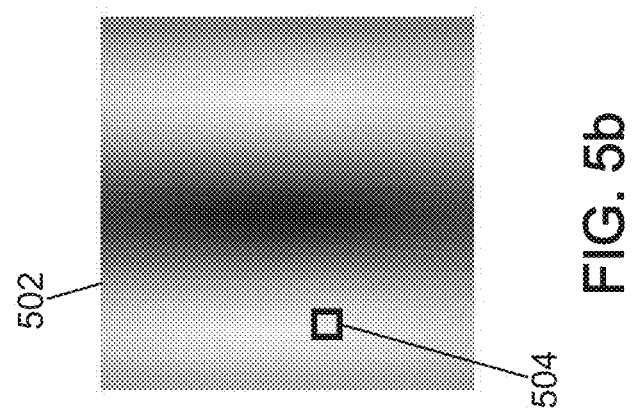
Figure 5A:
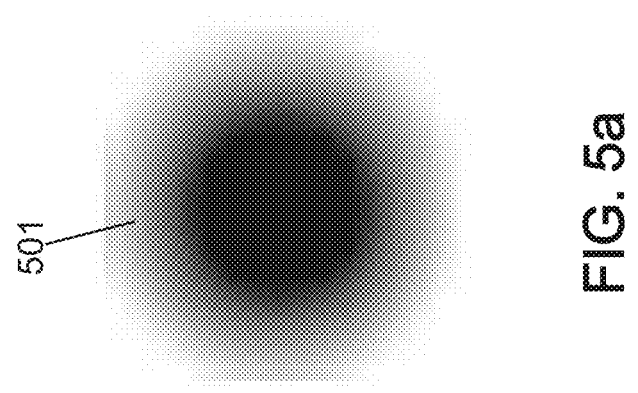

FIGS. 5a, 5b, and 5c are a set of examples of weighting matrix (or kernel) used in the integration process (see FIGS. 3a to 4).

As indicated above, it is possible to determine for each pixel of a group of pixels (of the retina sensor) a weight w associated with said pixel.

Said weight may be advantageously determined by a "kernel" or a weighting matrix.

For instance, if the group of pixels is a square, it is possible to use a kernel similar to the element 501, 502 or 503 (the "shape" of the kernel being changed). In the representation of FIG. 5c, if the pixel in the kernel is dark (element 505), the associated weight with said pixel is important. If the pixel in the kernel is light (element 504), the associated weight with said pixel is small.

For instance, a kernel similar to element 502 may be used to ease the detection of vertical pattern. A kernel similar to element 503 may be used to ease the detection of oblique pattern.

By changing the shape of the kernel, filtering operations can be implemented using an event-based convolutional network approach. Rather than changing the shape or the form of the kernel, different filter operations can be implemented by using different weighting matrices, for instance.

The kernel may be of any forms.

Expressions such as "comprise", "include", "incorporate", "contain", "is" and "have" are to be construed in a non-exclusive manner when interpreting the description and its associated claims, namely construed to allow for other items or components which are not explicitly defined also to be present. Reference to the singular is also to be construed in be a reference to the plural and vice versa.

A person skilled in the art will readily appreciate that various parameters disclosed in the description may be modified and that various embodiments disclosed may be combined without departing from the scope of the invention.

The invention claimed is:

1. A method for processing asynchronous signals generated by a light sensor, the sensor having a matrix of pixels, the method comprising:

receiving the asynchronous signals, each asynchronous signal being associated with a pixel in a group of pixels in the matrix, each signal comprising successive events issued by the associated pixel;

upon an occurrence of an event in one of the asynchronous signals, updating an integration value associated to said group by adding an additive value to the integration value;

if the integration value is greater than a predetermined threshold, generating an event in an outputted asynchronous signal.

2. A method according to claim 1, wherein the method further comprises:

decreasing the integration value according to a time-dependent function.

3. A method according to claim 1, wherein the additive value is selected from the group consisting of:

a predetermined value;

a value function of a predetermined value and a weighting parameter function of a position in the group of the pixel from which the occurred event is issued;

a value function of an information of gray level associated with the occurred event; and a value function of a value function of an information of gray level associated with the occurred event and a weighting parameter function of a position in the group of the pixel from which the occurred event is issued.

4. A method according to claim 1, wherein the method further comprises:
sending the outputted asynchronous signal to a pixel of a retina implant.

5. A method according to claim 1, wherein the method further comprises:
upon the generation of the event in the outputted signal, setting the integration value to 0.

6. A method according to claim 1, wherein the method further comprises:
upon the generation of the event in the outputted signal, setting the integration value to a value corresponding to the difference of the integration value and the predetermined threshold.

7. A method according to claim 1, wherein the predetermined threshold is function of a number of pixels in the group of pixels.

8. A non-transitory computer readable storage medium, having stored thereon a computer program comprising program instructions, the computer program being loadable into a data-processing unit and adapted to cause the data-processing unit to carry out the steps of claim 1 when the computer program is run by the data-processing unit.

9. A retinal device, the device comprising:
a light sensor, the sensor having a matrix of pixels,
a circuit for:
receiving the asynchronous signals, each asynchronous signal being associated with a pixel in a group of pixels in the matrix, each signal comprising successive events issued by the associated pixel;
upon an occurrence of an event in one of the asynchronous signals, updating an integration value associated to said group by adding an additive value to the integration value;
if the integration value is greater than a predetermined threshold, generating an event in an outputted asynchronous signal.

10. A method according to claim 2, wherein the additive value is selected from the group consisting of:
a predetermined value;
a value function of a predetermined value and a weighting parameter function of a position in the group of the pixel from which the occurred event is issued;
a value function of an information of gray level associated with the occurred event; and
a value function of a value function of an information of gray level associated with the occurred event and a weighting parameter function of a position in the group of the pixel from which the occurred event is issued.

11. A method according to claim 2, wherein the method further comprises:
sending the outputted asynchronous signal to a pixel of a retina implant.

12. A method according to claim 3, wherein the method further comprises:
sending the outputted asynchronous signal to a pixel of a retina implant.

13. A method according to claim 2, wherein the method further comprises:
upon the generation of the event in the outputted signal, setting the integration value to 0.

14. A method according to claim 3, wherein the method further comprises:
upon the generation of the event in the outputted signal, setting the integration value to 0.

15. A method according to claim 4, wherein the method further comprises:
upon the generation of the event in the outputted signal, setting the integration value to 0.

16. A method according to claim 2, wherein the method further comprises:
upon the generation of the event in the outputted signal, setting the integration value to a value corresponding to the difference of the integration value and the predetermined threshold.

17. A method according to claim 3, wherein the method further comprises:
upon the generation of the event in the outputted signal, setting the integration value to a value corresponding to the difference of the integration value and the predetermined threshold.

18. A method according to claim 4, wherein the method further comprises:
upon the generation of the event in the outputted signal, setting the integration value to a value corresponding to the difference of the integration value and the predetermined threshold.

19. A method according to claim 5, wherein the method further comprises:
upon the generation of the event in the outputted signal, setting the integration value to a value corresponding to the difference of the integration value and the predetermined threshold.

20. A method according to claim 2, wherein the predetermined threshold is function of a number of pixels in the group of pixels.

* * * * *